United States Patent [19]
Ziekman et al.

[11] 4,055,382
[45] Oct. 25, 1977

[54] TESTING METHOD FOR THE SEPARATE DETERMINATION OF VARYING WORK SURFACE FLAWS AND ARRANGEMENT FOR SAID METHOD

[75] Inventors: Paul Ziekman, Bilthoven; Jan A. P. van Riet, Nieuwegein, both of Netherlands

[73] Assignee: SKF Industrial Trading and Development Company, B.V., Nieuwegein, Netherlands

[21] Appl. No.: 652,734

[22] Filed: Jan. 27, 1976

[30] Foreign Application Priority Data

Jan. 29, 1975 Netherlands .................... 7501009

[51] Int. Cl.² ............................................. G01N 21/48
[52] U.S. Cl. ..................................... 356/210; 250/563; 250/572; 356/241
[58] Field of Search ................. 356/73, 120, 209, 235, 356/241, 210; 250/562, 563, 572, 225

[56] References Cited

U.S. PATENT DOCUMENTS

| 3,749,496 | 7/1973 | Hietanen et al. ............ 356/73 |
| 3,806,256 | 4/1974 | Ishak ............................ 356/209 X |
| 3,924,954 | 12/1975 | Decret et al. ................ 250/227 X |

FOREIGN PATENT DOCUMENTS 2,112,229 10/1971 Germany ...................... 356/120

OTHER PUBLICATIONS

Heinz, "Method of Checking Wall Imperfections," Western Electric Technical Digest, No.19, pp. 31-32, July, 1970.

Primary Examiner—John K. Corbin
Assistant Examiner—Matthew W. Koren
Attorney, Agent, or Firm—Daniel M. Rosen

[57] ABSTRACT

A process and apparatus for the automatic checking of machined part surfaces for surface flaws by means of bundled light rays which are directed onto the surface to be checked by means of optical instruments, whereby the light rays are reflected by the surface with varying intensity and in accordance with the nature of the surface, and whereby the light rays, at least partly, are redirected via optical instruments towards at least one light-sensitive element which converts the reflected light energy into electrical signals, and the step of separately evaluating the reflected amount of light as far as its varying intensity and dispersion is concerned, in order to indicate surface flaws of different types, as for example, material and machining flaws.

5 Claims, 6 Drawing Figures

TESTING METHOD FOR THE SEPARATE DETERMINATION OF VARYING WORK SURFACE FLAWS AND ARRANGEMENT FOR SAID METHOD

The invention relates to a method and apparatus for automatically checking machined work surfaces. In arrangements for checking machined work surfaces for surface flaws, bundled light rays are directed onto the surface to be tested by means of optical instruments, in a manner such that light rays are reflected by the surface with a varying degree of intensity. The light rays are, at least partly, redirected via the aforesaid optical instruments to at least one light-sensitive element converting the reflected amount of light into electrical signals.

In arrangements such as described above, the surface flaws are subdivided into so-called material flaws and machining flaws some of these flaws are regarded as permissible in specific cases while others are classified as not permissible. The material flaws are subdivided into single and multiple porosity flaws. The machining flaws or defects may be still existent drilling or boring traces or those flaws resulting from grinding or faulty grinding traces.

The above described arrangement for the checking or testing machined work surfaces as to possible surface flaws by means of light in connection with optical and electrical instruments is known from the German Pat. Application 2,412,763 and the U.S. Pat. No. 3,761.186. Both are examples of known devices permitting the checking of bore interior surfaces for surface imperfections wherein the light rays projected onto the surface are moved in longitudinal as well as also in a circumferential direction of the bore in question. Such arrangements, however, are only capable of generally detecting surface blemishes indicating same by monitors. The question of what type of defect is present is not answered by the aforementioned devices. The question as to what type of defect has been detected, however, is of the utmost importance, because only then is it possible to rapidly determine the cause for such defects. With the above described devices, the question obviously can only be answered by a manual sorting of the faulty workpieces and by a subsequent ocular inspection - if necessary with the help of suitable measuring instruments.

It is therefore the prime object of the present invention to provide a trouble-free and simple testing method which permits the automatic detection of surface flaws or imperfections which, because of their origin, are of a different nature, and to provide a novel and unique apparatus for performing the aforesaid procedure.

The foregoing object is achieved, according to the invention, by utilizing the reflected amount of light which, because of its varying degree of intensity and area of impact, is determined separately for the detection and indication of surface blemishes and defects on a different nature, e.g. material and machining defects.

In accordance with a preferred testing method in accordance with the present invention, the bundled light rays constitute parallel laser rays vertically directed onto the subject work surface by means of optical equipment, while simultanesouly moving the light rays in relation to the work surface.

When checking a work surface which may be the inner wall of a bore it is a further advantageous embodiment of the invention to effect the relative movement of light rays in such a way that the projection of the light rays follows a helical path on the inner surface of the bore, whereby the pitch of the helix is less than the maximal fixed permissible dimension of a surface flaw.

In a still further embodiment of the invention, an especially advantageous arrangement for the application of said test method has been created by combining two different systems of optical instruments for the separate detection of surface flaws of a different nature, e.g. material and machining defects. One system, on one hand, is provided with a prism which disperses or splits the light rays and permits passage of part of the bundled rays coming from a source of energy in one direction, while deflecting them in the opposite direction. Also in line with the direction of the rays, there is a first lens, a deflector mirror, and a second lens confocally arranged in relation to the other lens so that the projected light rays will hit the surface to be tested in the parallel direction. The system, on the other hand, has an objective which leads at least part of the amount of light reflected onto the mirror by the second lens, from the surface to be tested, and arrived at the first lens, to a light sensitive element arranged behind the objective. The light sensitive element can take the form of a photodetector for the purpose of detecting such material flaws. The second system has several light-transmitting fibers whose inlets have been arranged on the circumference of a ring surrounding the second lens, and whose ends lead into an annular member confronted by a corresponding member, whereby said member likewise has lightsensitive elements in the form of photodetectors for the detection of machining flaws.

Further details and suitable improvements have been described and explained below and shown schematically in the drawing, wherein FIG. 1 is an arrangement for carrying out the test process according to the invention in a perspective view;

Figure 1:
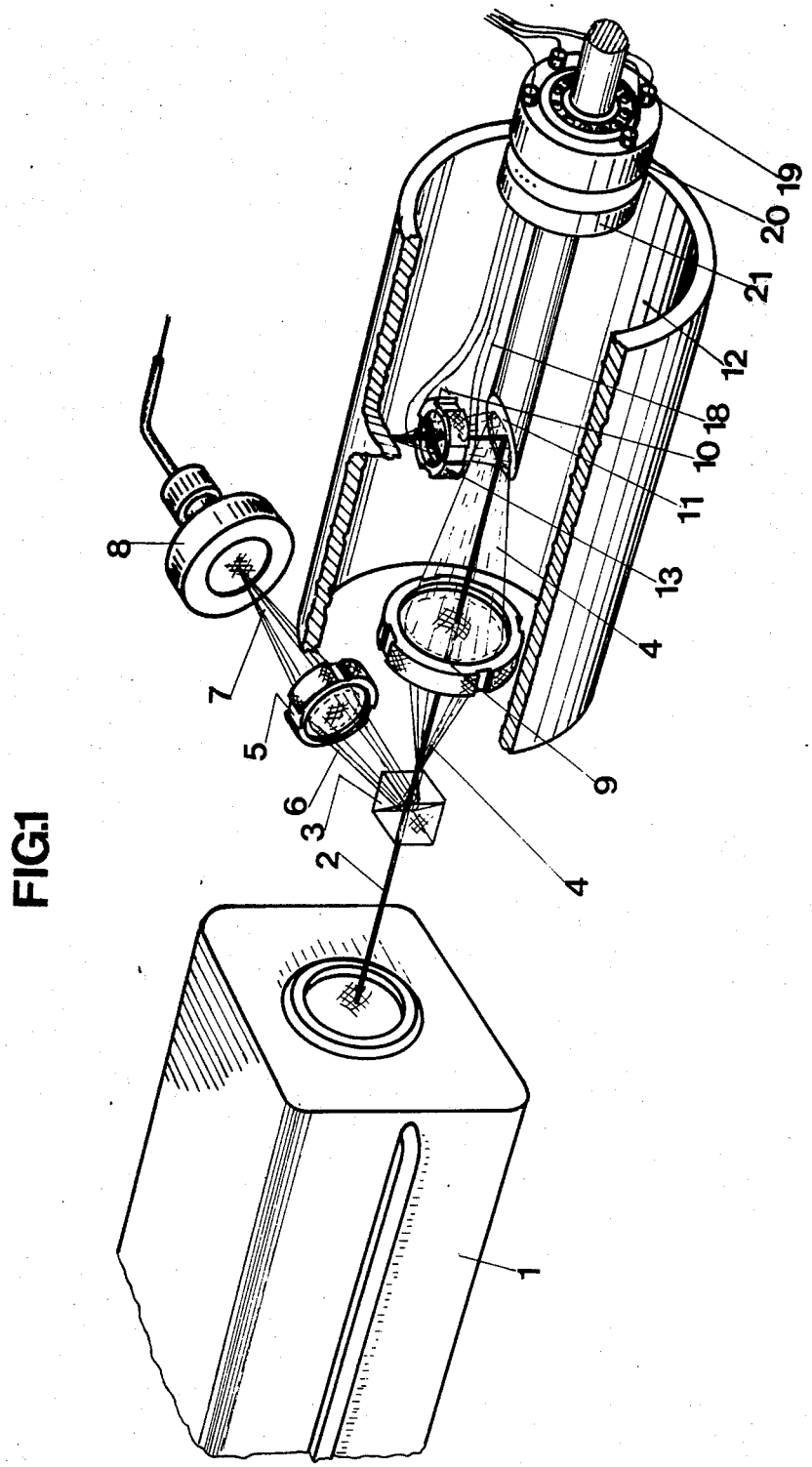

The arrangement shown in FIG. 1 for the testing of surface defects has an energy source 1 which generates a parallel bundle of light, in the present arrangement laser beams 2. A beam splitter such as a light dispersing prism 3, more commonly termed a beam splitting prism, permits the laser beam 2, in essence, to pass in one direction, but which, however, vertically deflects an essential portion of the reflected beams — here indicated by delimiting lines 6 — in the opposite, other direction, towards an objective 5 — here shown by a diverging bundle of light 6. The deffected beams portion then arrives, coming from said objective 5 and indicated by a converging bundle of light 7, at another light-sensitive element, in the present case a photodetector 8. The arrangement shown, furthermore, — following the path of the rays — coming from the energy source — has a planconvex lens 9, a deflecting mirror 11, and another planconvex lens 10, both of which lenses being rotatably mounted. The optical instruments 3, 5, 8, and 9, 10, 11, together form a primary system for the detection of material flaws on the inner surface 12 of a cylinder.

The detection process described above is effected in the following manner: The light bundle 2 coming from the source of energy 1 which has a cross sectional area of approx. 1 mm² first traverses the prism 3, whereby part of the light is deflected, while the residual part of the light passes through the prisms without any obstruction, and finally strikes the deflection mirror 11 inclined 45° in relation to the optical axis, via the planconvex lens 9. From the deflection mirror 11, the laser beams, through the second planconvex lens, are then radiated onto the surface 12 to be tested. The irradiated surface 12 of the cylinder's inner wall has approximately the same dimensions as the original cross sectional area of the laser beam 2. Furthermore, the light rays strike the surface in a parallel arrangement, a fact achieved by a confocal arrangement of the two lenses 9 and 10. This, however, does not mean that the detection sensitivity for the determination of such flaws is also approximately the same. The reason therefor is that the actually resulting intensity profile corresponds to a Gaussian distribution, illustrated as a nomogram, or graph of arithmetical probabilities. Should, however, a greater degree of sentitivity be desired, i.e. if the diameter of the scanning light spot should be smaller than the diameter of the light bundle coming from the source of energy, it will also be possible to arrange lenses 9 and 10 in a non-confocal setup, and with an increased distance between them.

The arrangement shown here as an example has been especially designed to check the interior surfaces of bores in cast parts for engines, where the minimum limit for porosity defects to be detected ranges around 0.25 mm, so that the indicated degree of sensitivity will generally suffice.

In the embodiment shown in FIG. 1 the problem is an inspection of the inner surface of a cylinder. For this purpose, the optical instruments 3, 5, 8, 9, 10, and 11 are moved in relation to the inner cylinder wall in such a way that the projection of the laser beams on the inner wall 12 describes a helical path, whereby, generally, the pitch of the curve should be less than the maximal permissible dimension of a surface flaw. In the present arrangement, e.g., said pitch amounts to 0.1 mm and, as mentioned before, only porosity defects are to be detected which have a minimal diameter of approx. 0.25 mm. This means that a possible porosity might be registered more than once.

Registration is effected by means of a photodetector 8 which receives specific amounts of varying degrees of intensity via the optical instruments 10, 11, 9, 3, and 5, depending on whether a greater or a lesser portion of the laser bundle striking the surface 12 to be cheked has been reflected towards lens 10 by said surface. In this connection it should be mentioned that the total aperture of the optical system 10, 11, 9, 3, 5, and 8 can be optimally used if the lens 10 is arranged as closely as possible to the area of the surface 12 under observation, i.e. if a maximal amount of the reflected light is absorbed. The foregoing arrangement also provides a higher so-called interference distance.

The photodetector is connected to an electronically operating device not shown here, whereby said device evaluates the signals arriving from the photodetector 8 and displays them in the form of readings.

Figure 2A:
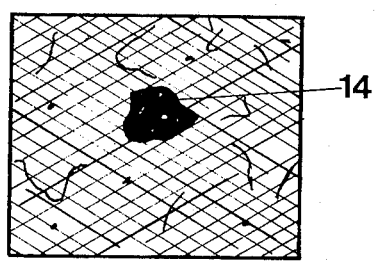
FIGS. 2A and 2B shows one section each of a work surface in an enlarged scale showing single and multiple porosity flaws respectively.
Figure 2B:
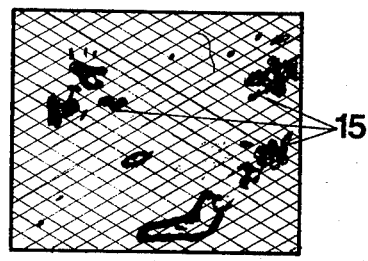

Examples of some material defects, as e.g. simple or multiple porosity defects 14 and 15 respectively have been shown in FIGS. 2A and 2B in approx. tenfold enlargement. These defects may be caused by bubbles forming in the material during casting, whereby such defects then come to the surface because of machining. The irregular surface of such a flaw is situated in a recess of the ideal interior cylinder wall surface. This means that the surface of such flaws will appear darker than its environment, so that less light will be reflected from this part of the surface. Furthermore, the irregular structure of this flaw surface causes the light to be reflected in various directions. If the light beam, along its rotational path, should strike a porosity of that type, then the primary optical system 10, 11, 9, 3, and 5 will conduct a lesser amount of light towards the photodetector 8 than would emanate from a perfect area of said surface.

Figure 4:
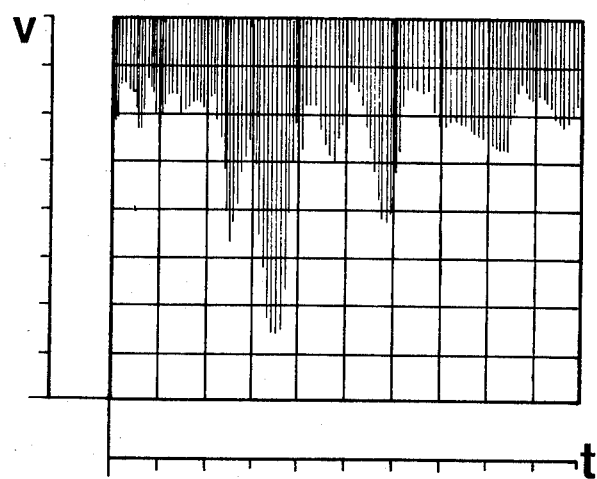
FIG. 4 is a diagram showing the impulse path of a photodetector indicating existing material flaws.

The resulting voltage generated by the photodetector will then vary, as shown in the diagram in FIG. 4. In FIG. 4, time is indicated on the abscissa, and the voltage V generated by the photodetector is indicated on the ordinate.

The vertically inscribed lines stand for negative voltage peaks per time unit, whereby their lengths in each instance constitute one unit of measure for the dimension of one flaw or defect. With the help of the electronic device not shown here it is then easy to determine whether the size, number, concentration etc. of the detected porosities exceed certain threshold limits or not.

As mentioned before, the individual defects are registered more than onec. The counting of voltage peaks occurring in sequence, generated by a porosity flaw, enables the electronic device to correctly interpret the obtained data. Furthermore, FIG, 4 demonstrates that during a first revolution along a porosity a relatively minor voltage peak will occur, since a relatively large portion of the bundle of rays will first scan over a "perfect" surface, and thus only a minor portion of the bundle will actually strike the flaw.

Figure 3A:
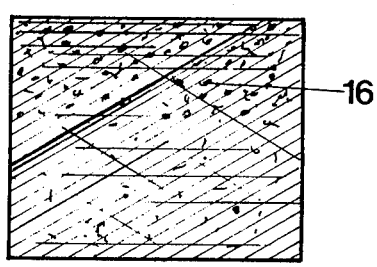
FIG. 3A shows a sectional view of a work surface in an enlarged scale with existing machining defects in the shape of grinding traces.

For the simultaneous detection of material and machining flaws, i.e. boring traces 16 (FIG. 3A) the arrangement according to the invention (FIG. 1) also provides a secondary system having several light-transmitting fibers 18, with their one ends arranged on the circumference of a ring 13 surrounding the second lens 10, and whose other ends terminate in a ringshaped member 21, opposite which a corresponding member 20 has been arranged carrying a number of photodetectors 19. The annular member 21 thereby has been rotatably mounted together with optical instruments 9, 10, 11, and 18 while the member 20 cannot be rotated.

In contrast to the earlier described primary system designed to detect material flaws by measuring the total intensity of the reflected light, the secondary system measures the spatial intensity distribution of the light for the purpose of measuring machining flaws or defects. Detection of the spatial intensity distribution of the light is made possible by the fiber-optical elements arranged on the circumference of the lens 10 on a ring 13, whereby these elements transmit their information in a non-contacting manner to the photodetectors 19.

Figure 3B:
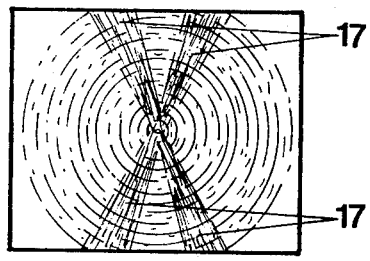
FIG. 3B is a representation for the demonstration of a so-called diffraction pattern.

The photodetectors, on the other hand, are connected with an electronically operating device not shown here which compares the incoming electrical signals with those of a diffraction pattern obtained from a perfect surface. FIG. 3B shows a diffraction pattern of a perfect surface. If, e.g., a well-machined surface area of 1 mm² is irradiated, and if the reflected light then is brought in contact with a light-sensitive (photographic) plate, the result will be a diffraction pattern as shown in FIG. 3B, wherein distinctly higher light intensity is found than in the other areas. If, however, there are still some drill marks left, (FIG. 3A) or the surface has not been immaculately ground, a diffraction pattern diverging from that in FIG. 3B will be the result. The different diffraction patterns are then compared by the electonic device and — depending on whether said flaws are considered permissible or not —indicated by the aforesaid device.

The present invention has only been explained with regard to one single embodiment for the detection of surface flaws in a cylindric bore, however, it it also possible to check several surfaces of a part by means of several separate light rays and the necessary optical instruments and lightsensitive elements on a fixed-cycle conveyer belt, and, subsequently to the checking operation, to eliminate the parts found to contain flaws in accordance with a fixed permissible flaw quota and divert them to a second conveyor. Furthermore it is possible to check flat surfaces as well as such of any other nature for flaws with the aforesaid principle in accordance with the invention.

What is claimed is:

1. A method for the automatic checking of machined part surfaces for surface flaws comprising the steps of confocally directing a plurality of parallel bundled light rays onto the surface to be checked by means of optical instruments, whereby said light rays are reflected by said surface with varying intensity and in accordance with the nature of said surface, redirecting a portion of said light rays, via said optical instruments, towards at least one light-sensitive element which converts the reflected light energy into electrical signals, and further including the step of separately evaluating the reflected amount of light, for variation in intensity and dispersion, in order to indicate a plurality of different types of surface flaws.

2. The method according to claim 1 wherein said bundled light rays constitute parallel laser beams which are vertically directed onto that part of the surface to be checked by means of optical instruments whereby said light rays simultaneously perform a motion relative to said surface part.

3. The method according to claim 2 wherein said relative motion during said surface checking of a part of workpiece constituting the inner surface of a bore is performed in such a way that the projection of the light rays on the inner surface follows a helical path, whereby the pitch of the helical path is less than the major fixed permissible dimension of a surface flaw.

4. An apparatus for indicating machined surface flaws including material and machining flaws comprising first and second systems of optical instruments for detection of surface flaws separately, one of said systems comprising a source of light energy, a beam splitting prism splitting a portion of the light rays coming from said source of energy as a bundle to pass through in one direction, while deflecting a portion of said light in a second direction, the path of said one direction including a first lens, a deflecting mirror, and a second lens, said second lens being arranged confocally with said first lens, thereby permitting the light rays incident thereon to strike said surface to be tested in a parallel arrangement, said one of said systems further including an objective which transmits at least part of the amount of light reflected by said surface to be checked via said second lens onto said mirror to said first lens, and deflected from said beam splitting prism to a photosensitive element, said photosensitive element being in the form of a photodetector for detecting said material flaws, and the other of said systems having a plurality of fiberoptic elements whose one ends have been arranged on the circumference of a ring surrounding said second lens, their other ends being terminated in an annular member, confronted by a correspondingly shaped member, and which also carries further photosensitive elements in the form of photodetectors for the purpose of detecting machining flaws.

5. The arrangement in accordance with claim 4, wherein said annular member, together with said optical instruments, has been rotatably mounted whereas said correspondingly shaped member remains stationary.

* * * * *

UNITED STATES PATENT OFFICE
CERTIFICATE OF CORRECTION

Patent No. 4,055,382                    Dated October 25, 1977

Inventor(s) Paul Ziekman et al.

It is certified that error appears in the above-identified patent and that said Letters Patent are hereby corrected as shown below:

Column 2, line 40 change "shows" to --show--.

Column 2, line 58 change "6" to --4--.

Column 2, line 60 change "deffected" to --deflected--.

Column 3, line 28 after "arrange" insert --the--.

Signed and Sealed this

Fourth Day of July 1978

[SEAL]

Attest:

RUTH C. MASON
Attesting Officer

DONALD W. BANNER
Commissioner of Patents and Trademarks